United States Patent [19]
Abraham et al.

[11] Patent Number: 5,303,030
[45] Date of Patent: Apr. 12, 1994

[54] METHOD AND APPARATUS FOR MONITORING AND MEASURING THE SURFACE TENSION OF A FLUID USING FIBER OPTICS

[75] Inventors: Bernard M. Abraham, Oak Park; John B. Ketterson, Evanston; Thomas M. Bohanon; John M. Mikrut, Evanston, all of Ill.

[73] Assignee: Northwestern University, Evanston, Ill.

[21] Appl. No.: 801,153

[22] Filed: Dec. 2, 1991

[51] Int. Cl.[5] .................................................. G01B 9/02
[52] U.S. Cl. .................................... 356/345; 356/357; 356/358
[58] Field of Search ........................ 356/345, 357, 358; 250/227.19, 227.27

[56] References Cited

U.S. PATENT DOCUMENTS

| | | |
|---|---|---|
| 4,512,183 | 4/1985 | Alexander . |
| 4,611,486 | 9/1986 | Stockhausen . |
| 4,677,298 | 6/1987 | Zelmanovic et al. . |
| 4,737,035 | 4/1988 | Aoki et al. . |
| 5,005,005 | 4/1991 | Brossia et al. . |
| 5,005,401 | 4/1991 | Pierce et al. . |

FOREIGN PATENT DOCUMENTS 1516775 10/1989 U.S.S.R. ............................... 356/345

OTHER PUBLICATIONS

Landau, L. D., et al., "Fluid Mechanics", Institute of Physical Problems, U.S.S.R. Academy of Sciences, vol. 6, of Course of Theoretical Physics, Pergamon Press, pp. 237-241.

Sohl, C. H., et al., "Novel Technique for Dynamic Surface Tension and Viscosity Measurements at Liquid-Gas Interfaces", Dept. of Physics, N. W. Univ., Evanston, Ill. & Argonne Nat. Lab., May 1978, pp. 1464-1469.

Hansen, Robert S., et al., "Waves at Interfaces", pp. 2-57.

Halperin, K. et al., "A Study of the Mechanical Behavior of Surface Monolayers Using Orthogonal Wilhelmy Plates", Dept. of Materials Science . . ., N.W., Univ., Ill., 1988, pp. 161-164, Langmuir, vol. 5, No. 1, 1989.

Chen, Yes-Lane et al., "Static and Dynamic Properties of Pentgadecanoic Acid Monolayers at the Air-Water Interface", School of Pharmacy & Dept. of Chem. Univ., of Wis., 1986, Langmuir, vol. 2, 1986, pp. 349-354.

Miyano, Kenjiro, "Local Mechanical Properties of Monomolecular Films on Water Measured with a Capillary Wave Probe", Dept. of App. Phy., Univ. of Tokyo, Japan, Langmuir, vol. 6, No. 7, 1990, pp. 1254-1259.

Primary Examiner—Samuel A. Turner
Attorney, Agent, or Firm—James A. Scheer

[57] ABSTRACT

A non-contact method and apparatus for measuring and monitoring the surface of a fluid using fiber optics and interferometric detection to permit measurement mechanical characteristics' fluid surfaces. The apparatus employs an alternating electric field gradient for generating a capillary wave on the surface of the fluid. A fiber optic coupler and optical fiber directs a portion of a laser beam onto the surface of the fluid, another portion of the laser beam onto the photo sensor, and directs light reflected from the surface of the fluid onto the photo sensor. The output of the photo sensor is processed and coupled to a phase sensitive detector to permit measurement of phase shift between the drive signal creating the capillary wave and the detected signal. This phase shift information is then used to determine mechanical properties of the fluid surface such as surface tension, surface elasticity, and surface inhomogeneity. The resulting test structure is easily made compact, portable, and easy to align and use.

15 Claims, 4 Drawing Sheets

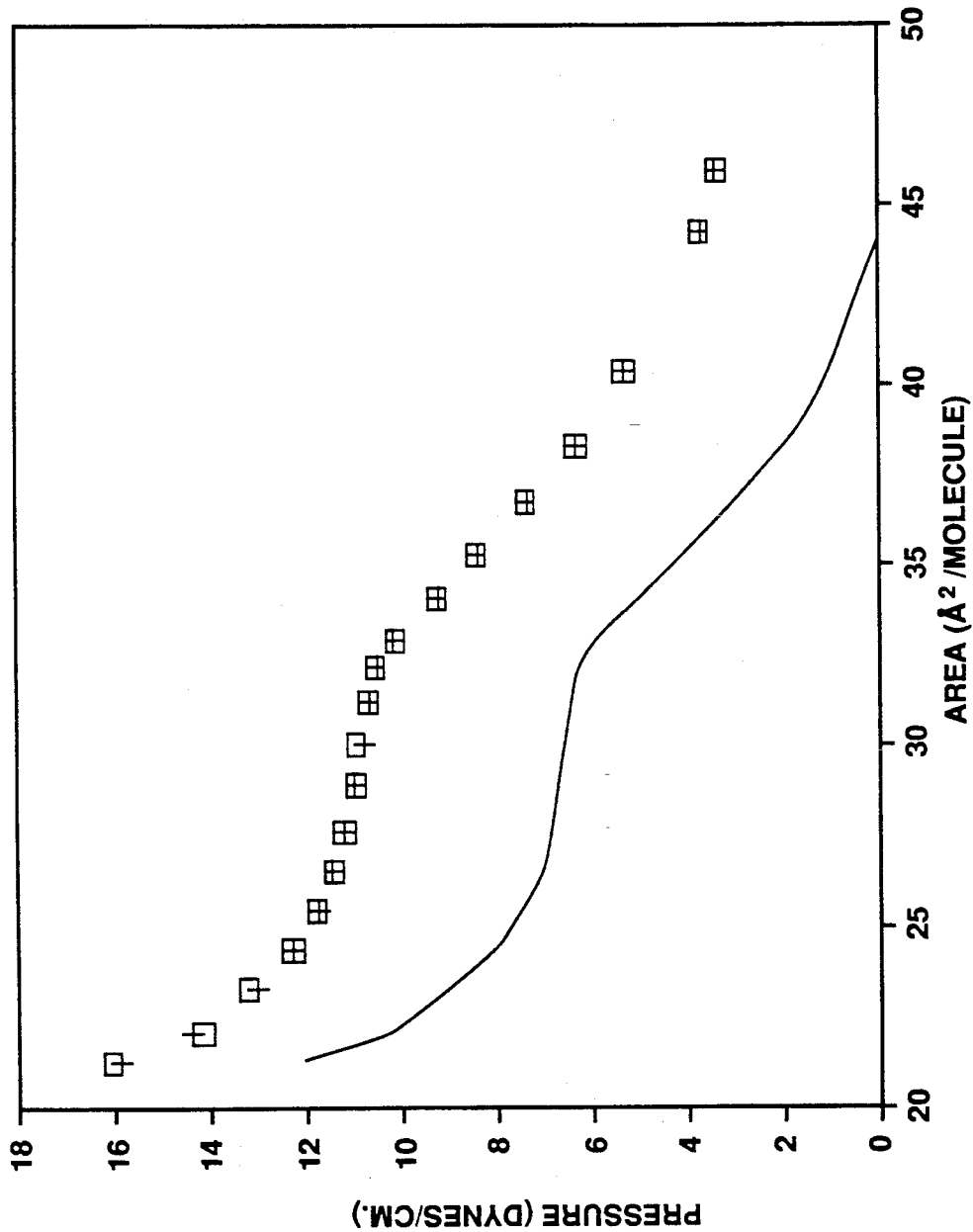

METHOD AND APPARATUS FOR MONITORING AND MEASURING THE SURFACE TENSION OF A FLUID USING FIBER OPTICS

This invention was made with Government support under Grant Number DE-FG02-84ER45125 awarded by the Department of Energy. The Government has certain rights in the invention.

BACKGROUND OF THE INVENTION

This invention relates generally to the field of measuring and monitoring the characteristics of fluids and more particularly to a non-contact method and apparatus for monitoring the surface of a fluid using fiber optics which enables the determination of mechanical properties of fluids such as the surface tension.

There are a variety of methods for measurement of the surface tension of fluids which are known in the art. In the known Wilhelmy plate technique, a plate is placed in contact with the fluid surface, and is then withdrawn from the surface. The maximum force needed to break the plate away from the surface is measured to determine the fluid surface tension. This approach requires contact in the surface, and thereby disturbs the characteristics of the fluid and obstructs the flow of the fluid such that surface tension at the plate may not be the same as that away from the plate. In the case of thin films, the contact and removal of the plate may damage the film, and in the case of some rigid or viscous films, the plate may be forced away from the vertical, providing erroneous readings.

Another known approach to measurement of surface tension is the Langmuir balance technique which permits a differential measurement. In this technique, a float and flexible barrier divides a fluid surface into two regions: one region with a clean surface and one region with a surface covered with an insoluble film, the surface tension of which is to be measured. The float senses the differential force between the two regions. The float is coupled to a force measurement device permitting measurement of the average difference of the surface tension between the clean surface and film covered surface. This approach can only measure the gross average difference and can only measure surface tension at the boundary of the fluid, and thus can provide no information about inhomogeneity. In addition, the apparatus must be custom designed to fit a particular test fixture, and its position must be fixed. In addition, the Langmuir technique only measures a difference in surface tension, can only be used in uniaxial compression, and requires contact with the fluid, thereby introducing errors.

The capillary wave measurement technique can be used to determine surface tension without contacting the surface. This technique utilizes a capillary wave generator to produce capillary waves on the fluid surface. A beam of light is directed using lenses and mirrors onto the surface. The reflected light is then detected and analyzed to determine the surface tension of the fluid. Thus, this technique does not require contact with the film. However, the apparatus must be customized to accommodate the light sensing device and the lens/mirror structure needed to properly direct the light beams. Consequently, this method is difficult to implement, align, and use. In addition, such capillary wave instruments cannot be made easily portable.

Accordingly, it is an object of the invention to provide a novel non-contact method and apparatus for measurement of the surface tension of a fluid which employs the capillary wave technique, and which is portable and easy to use.

It is another object of the invention to provide a novel non-contact method and apparatus using interferometric detection for measurement of the surface tension of a fluid utilizing a fiber optic system.

It is another object of the invention to provide a novel non-contact method and apparatus using interferometric detection for measurement of the surface tension of a fluid which is compact and portable.

It is another object of the invention to provide a novel non-contact method and apparatus for monitoring the surface of a fluid using interferometric detection which does not require customizing to fit the test structure.

It is another object of the invention to provide a novel non-contact method and apparatus for monitoring the surface of a fluid using interferometric detection which is capable of monitoring and measuring a variety of fluid characteristics including surface tension, anisotropy of certain surface characteristics and changes in the elasticity of a surface film.

Briefly, according to one embodiment of the invention, apparatus and corresponding method are provided for monitoring the surface of a fluid. The apparatus comprises means for generating a surface wave on the surface of the fluid, a photo sensor for detecting optical energy, and optical means for generating a beam of optical energy, for example, a laser. A fiber optic coupling device coupled to the optical means directs a portion of the optical energy beam onto the surface of the fluid, another portion of the optical energy beam onto the photo sensor, and directs optical energy reflected from the surface of the fluid onto the photo detector. Means are provided to couple the photo detector to a phase sensitive detector to permit measurement of phase shifts indicative of surface tension changes and for determination of capillary wavelengths.

BRIEF DESCRIPTION OF THE DRAWINGS

The invention, together with further objects and advantages may be understood by reference of the following description taken in conjunction with the accompanying drawings.

FIG. 4 is a plot illustrating the isotherm of a pentadecanoic acid monolayer on water.

DETAILED DESCRIPTION OF THE INVENTION

Figure 1:
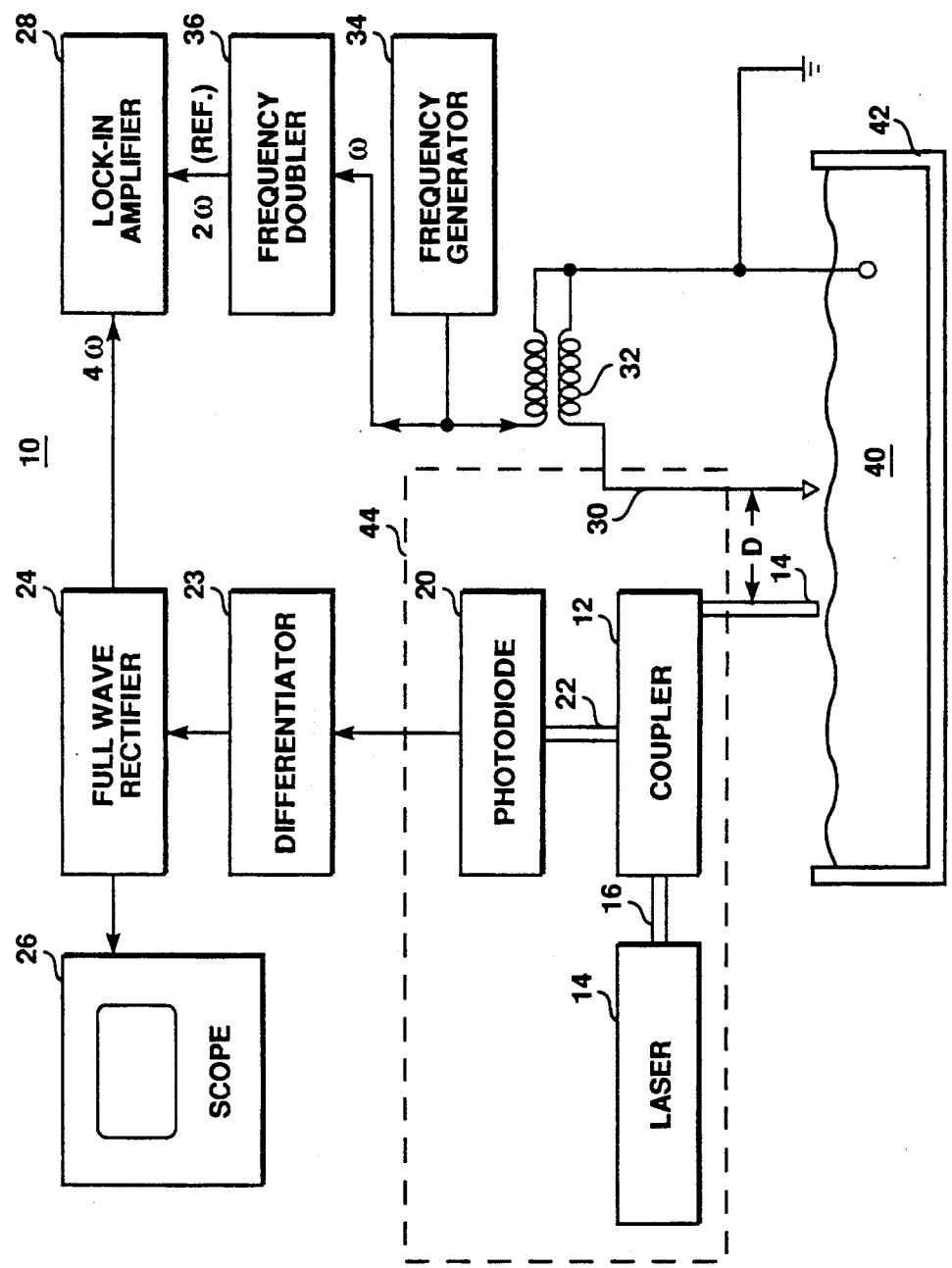
FIG. 1 is a detailed block diagram illustrating the overall structure and operation of the surface monitoring apparatus, according to the invention.

FIG. 1 is a detailed block diagram illustrating the surface monitoring and measurement apparatus 10 according to the invention. The apparatus 10 comprises a fiber optic coupler 12 (e.g., a conventional 3DB fiber optic coupler, Model 670-CF8, marketed by Gould, Inc., Glen Burnie, Maryland) including an output optical fiber 14 and an optical input 16, as shown. An optical energy beam generator 18, such as a neon helium laser or solid state laser, is coupled to the optical input 16 and a photo sensor 20 (e.g., conventional photo diode) is coupled to a second output 22 of the coupler 12. The output of the photo diode 20 is coupled to a differentiator circuit 23 and the output of the differentiator circuit 23 is coupled to a full wave rectifier 24 which is coupled to an oscilloscope 26. The full wave rectifier output is also coupled to a phase sensitive detector 28 (e.g., a Lock-In Amplifier, Model 5204, marketed by EE&G-Princeton Allied Research of Princeton, N.J.).

The apparatus 10 also comprises a variable frequency wave generator which includes a blade assembly 30 coupled through a transformer 32 to an adjustable frequency generator 34. The frequency generator 34 is also coupled to a frequency doubler 36 which is then coupled to the phase sensitive detector 28, as shown. The blade assembly 30 is maintained a short distance from the surface of a fluid 40 contained in fluid sample container 42 while the fluid 40 is maintained at ground potential, as shown. The blade assembly may, for example, be a single thin conductive foil. When a drive signal from the frequency generator is applied to the blade assembly 30, an alternating field is created which generates a capillary wave on the surface of the fluid.

In one compact and highly portable embodiment, the optical fiber 14, the optical energy source 18, the coupler 12, the photo sensor 20, and the blade assembly 30 are all mounted in a single mounting holder 44. The holder 44 permits the optical fiber 14 and the blade 30 to be held in fixed relationship to one another while alternatively permitting the fiber position to be adjusted and permitting the blade fiber combination to be moved to any position. The optical fiber 14 is oriented perpendicular to the plane of the fluid 40 and parallel to the plane of the blade 30. In one embodiment, the holder 44 may comprise a lucite block to which the blade assembly 30, laser 18, fiber 14, coupler 12, and sensor 20 are attached. The optical fiber may be attached to the lucite block using a conventional vertical and horizontal translators to permit separate adjustment of the distance (p) between the blade and fiber and the height of the fiber 14 above the fluid surface. In an alternative embodiment, the blade 30 may comprise two separate orthogonal blades with switches provided to switch the drive signal from one blade to the other to permit measurement in orthogonal directions.

Figure 2:
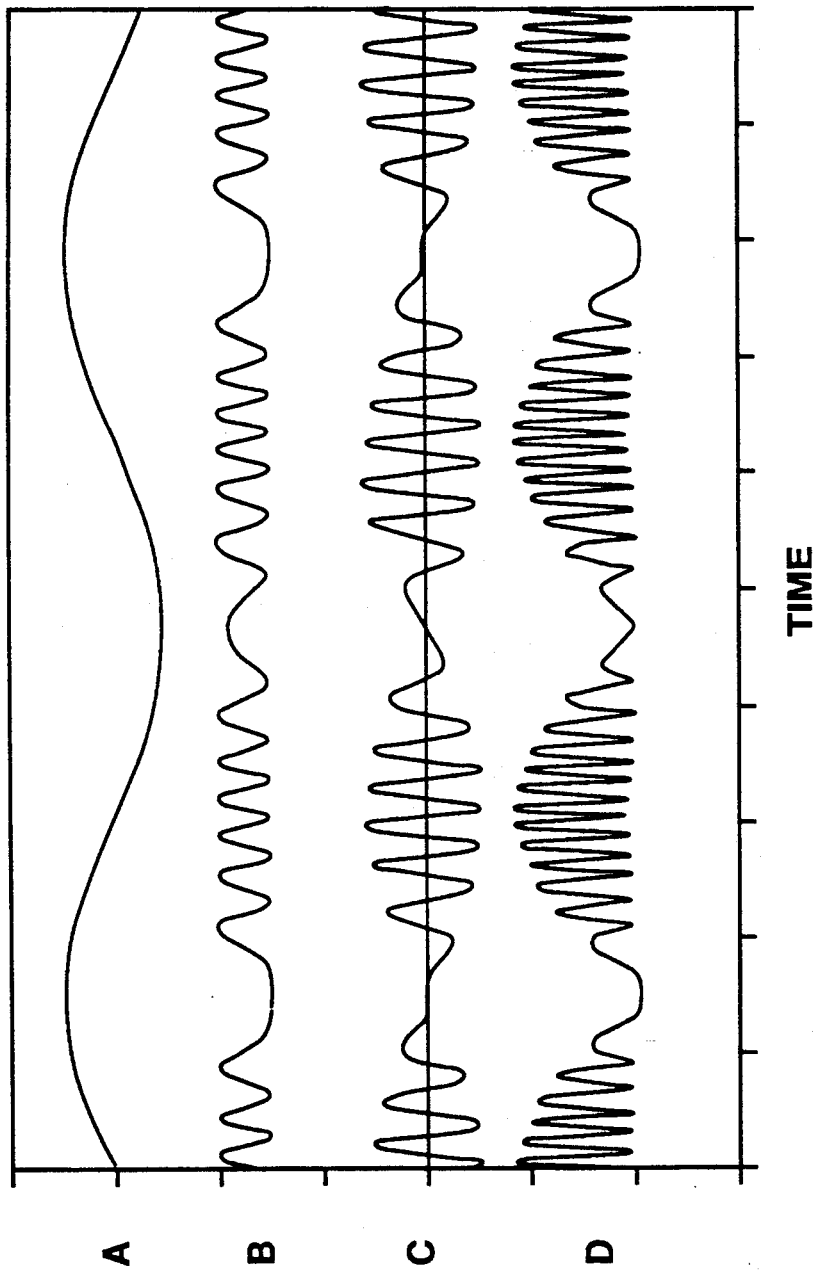
FIG. 2 is a plot of a set of wave forms illustrating signals at various points in the apparatus illustrated in FIG. 1.

In operation, a capillary wave is generated on the surface of the fluid 40 by bringing the blade 30 (e.g., platinum foil 0.25 mm thick by 25 mm long) in close proximity to the surface (e.g., approximately 0.5 mm) and applying a sinusoidal drive voltage (e.g., approximately 200-250 volts) of a selected frequency from the frequency generator 34 coupled through the transformer 32 while the fluid 40 is held at ground. The capillary wave generated by the alternating field gradient at the blade assembly 30 causes the fluid to rise on both the positive and the negative cycle generating a capillary wave with twice the frequency of the applied alternating field (i.e., twice the frequency of the drive signal from the frequency generator 34). In FIG. 2, curve A illustrates the resultant capillary wave. The blade and the fiber 14 are maintained at a fixed predetermined distance from one another (e.g., approximately 1 cm).

The optical source 18, which in one embodiment is a conventional one milliwatt helium neon laser coupled to the optical coupler 12 via a graded index rod lens, provides a beam of optical energy which is directed through the coupler 12 onto the surface of the fluid 40. In the illustrated embodiment, a beam of visible light is used although infrared or ultraviolet light may also be used.

The detection of the capillary wave is accomplished by interferometric detection. Thus, a portion of this light is reflected back from the end of the fiber 14 and another portion is reflected from the surface of the fluid 40 back into the fiber 14. Both portions of light are coupled through the coupler 12 back to the photo sensor 20 and are detected by the photo sensor 20. The photo sensor 20 generates a detected signal which is coupled to the differentiator circuit 23. In FIG. 2, curve B illustrates the interference signal generated at the photo sensor 20. The differentiator circuit 23 amplifies and differentiates the detected signal to produce a differentiated signal, as illustrated in curve C of FIG. 2. The differentiated signal is coupled to the full wave rectifier circuit 24 which full wave rectifies the differentiated signal to produce a rectified (effectively squared) differentiated signal, as illustrated in curve D of FIG. 2. This rectified signal is coupled to the oscilloscope 26 to permit the operator to observe the full wave rectified signal in order to ensure proper operation of the apparatus 10. The full wave rectified signal is also coupled to the phase sensitive detector 28 where it is compared to a reference signal coupled from the frequency doubler circuit 36. After differentiation and full wave rectification, the detected signal has an amplitude envelope at a frequency twice that of the capillary wave and therefore, the phase comparison between the applied signal and the detected signal is made at four times the generator frequency.

Accordingly, the frequency doubler circuit 36 doubles the drive signal which was used to drive the blade to produce the capillary wave to thereby generate the reference signal. The detector 28 compares the second harmonic of the reference signal to the full wave rectified signal to detect a phase difference ($\delta$) between the detected signal and the reference signal. In addition, a frequency counter may be used to provide a high accuracy value for the frequency of the frequency generator 34. In order to determine the surface tension of a fluid, the wavelength of the capillary wave is determined using the apparatus 10. To determine the surface tension for a film on the surface of a known fluid such as water, the phase shift (i.e., the change in wavelength) due to addition of the film is determined. This information may then be used to determine surface tension.

During detection, a portion of the optical beam ($E_1$) is reflected back from the end of the optical fiber 14 and a portion of the beam transmitted to the fluid surface ($E_2$) is reflected back from the fluid surface and retrieved through the coupler 12. The fluid reflected portion of the light $E_2$ is phase shifted with respect to the fiber end reflected portion $E_1$ by an amount proportional to twice the distance between the end of the fiber and the fluid surface. The resultant optical field applied to the photo sensor 20 is $$E = E_1 \cos wt + E_2 \cos [wt + \phi(t)]$$

This optical sum signal is detected by the photo sensor 20 to produce a detected voltage signal of approximately $$V \approx E^2 \approx E_1 E_2 \cos \phi(t)$$

Thus, the detected signal contains a component proportional to $\cos\phi(t)$ where $\phi(t)$ is the phase difference between $E_1$ and $E_2$. This phase difference $\phi(t)$ may be expressed as $$\phi(t) = 2\pi[d - a(t)]/\lambda$$

where d is the distance between the end of the fiber and the undisturbed fluid surface, and $\lambda$ is the light wavelength. Thus, the phase $\phi(t)$ is modulated by the time dependent amplitude of the capillary wave, $a(t) = A\cos\Omega t$ where A is the capillary wave amplitude and n is the frequency of the capillary wave.

The principle of light dispersion for a capillary wave is well known and may be utilized to determine surface pressure using the apparatus 10. The equation for the dispersion relationship for a capillary plane wave is well known. In the case in which the modulus of elasticity of a monolayer film being tested is equal to zero, the surface tension ($\sigma$) of the monolayer can be calculated from the Kelvin equation. The Kelvin equation may be expressed as $$\sigma = 2\rho\lambda_0^3/\pi T^3 = 2\rho D^3/\pi T^2 N^3$$

where T is the period of the frequency generator, $\lambda_0$ is the wavelength of the capillary wave, D is the path length between the capillary wave generating point (i.e., the blade 30) and the detection point on the surface, N is the number of wavelengths in the path length D, and $\rho$ is the density of water. In addition, regardless of the modulus of elasticity, the capillary wave apparatus 10 measurements show discontinuities in isotherms (i.e., plot of surface pressure vs molecular area) which indicates the occurrence of phase changes. If the modulus of elasticity is large, the surface tension calculated using the Kelvin equation is approximate while the more complete known equation for the dispersion relation may be used to determine a more accurate value for the surface tension.

To determine the surface tension for a fluid, the surface is scanned to determine the wavelength of the capillary wave. This can be done by determining the phase differences ($\delta$) between the drive reference signal and the detected signal with the optical fiber 14 at one position relative to the blade 30, then moving the fiber until a full wavelength change in phase has occurred, and measuring the distance, the fiber was moved to obtain the wavelength. Alternatively, a set of phase measurements (e.g., three) can be made at selected distances from the blade. These values may then be used to calculate the wavelength of the capillary wave. The wavelength may then be used in the Kelvin equation above to determine the surface tension.

To measure surface tension of a film on water, T and D are known, and $N_0$ is determined using the surface tension of pure water and varying the frequency, or by scanning. The phase $\delta$ is determined for the pure fluid, then the film is added and a change in phase $\Delta\delta$ is determined. Any change in the surface tension $\sigma$ (including changes due to other factors, such as temperature change, etc.) may then be calculated by measuring the change in phase $\Delta\delta$ caused by the change (e.g., the addition of the film to the water surface). Thus, the surface tension may be calculated using the following equation $$\sigma = 2\rho D^3/\pi T^2(N_o + \Delta\delta/4\pi)^3$$

where $N_o$ is the value of N on clear water. The phase difference between the applied signal and the detected signal is obtained by comparing the differentiated, full wave rectified (squared) photo sensor detected signal to the second harmonic of the doubled reference signal.

Figure 3:
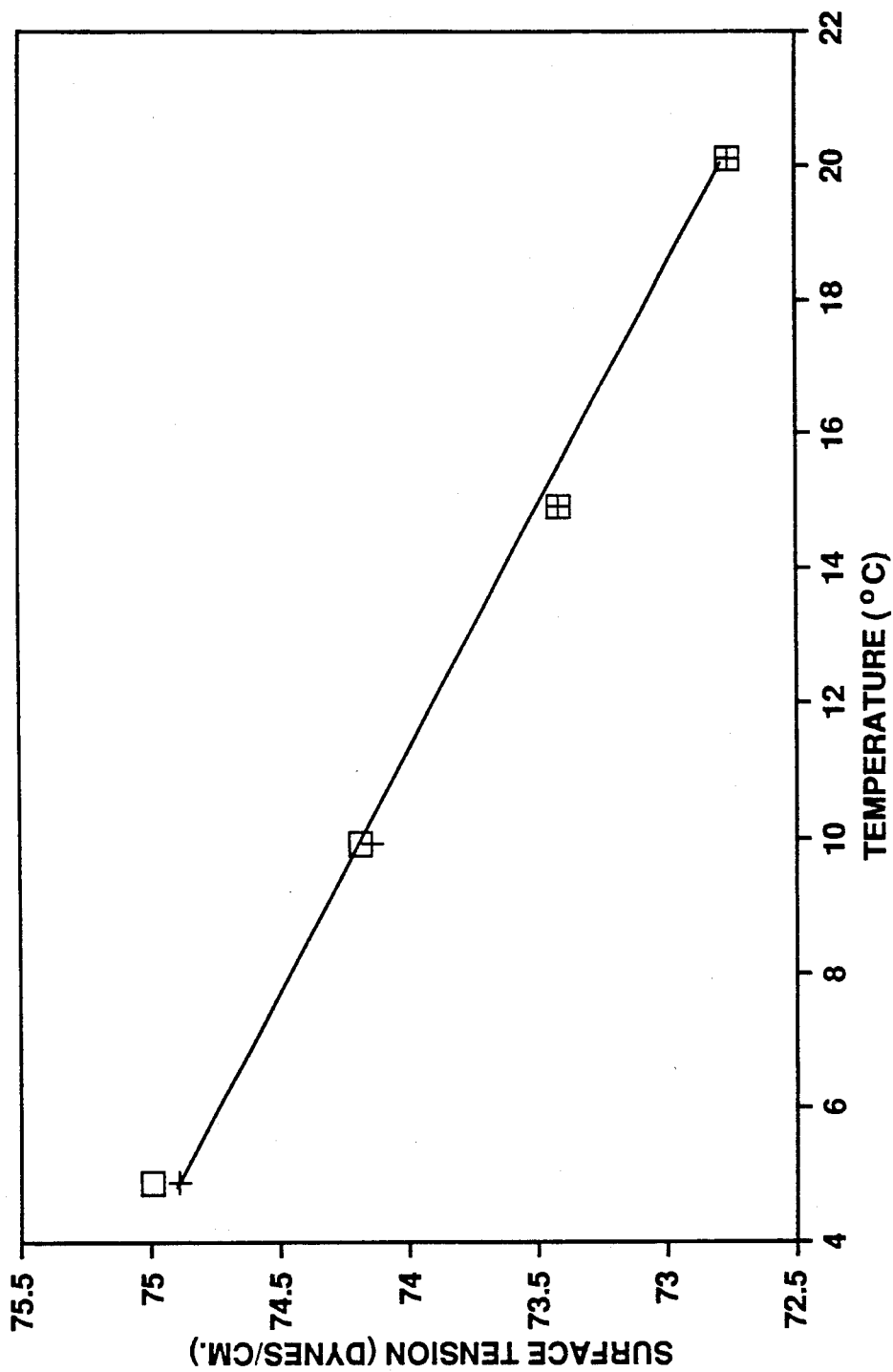
FIG. 3 is a plot illustrating determining surface tension values of pure water determined utilizing the invention.

FIG. 3 is a plot illustrating measurements of surface tension of water as a function of temperature made using the apparatus 10 (the Kelvin equation was used where $N_o$ was determined at 20° C.) along with accepted known values (+ indicates measured values). FIG. 3 illustrates that the apparatus 10 has sufficient sensitivity to determine temperature dependence of the surface tension of a fluid with accuracy.

FIG. 4 is a graph illustrating the isotherm of a pentadecanoic acid (PDA) monolayer at 23.0° C. on pH2 water. The results were determined using the Kelvin equation. The discrepancy between the surface pressure measured by the Wilhelmy plate and that calculated using the Kelvin Equation shows that PDA has a dynamic elasticity error at zero pressure.

Thus, the apparatus 10 can be used to measure various mechanical properties of fluids, or of a film on a fluid, including surface tension, and change in elasticity. By varying the distance between the blade and the optical fiber, damping information can be obtained. Also, viscoelastic information may be obtained as a function of frequency by varying frequency of the capillary wave.

Specific embodiments of the novel method and apparatus for monitoring and measuring the surface of a fluid have been described for the purpose of illustrating the manner in which the invention may be made and used. It should be understood that implementation of other variations and modifications of the invention in its various aspects will be apparent to those skilled in the art and that the invention is not limited by the specific embodiments described. It is therefore contemplated to cover by the present invention any and all modifications, variations, or equivalents that fall within the true spirit and scope of the underlined principals disclosed and claimed herein.

What is claimed is:

1. Apparatus for monitoring the surface of a fluid comprising:
    means for generating a surface wave on the surface of the fluid;
    means for producing an optical beam of optical energy;
    photo sensor for detecting optical energy and generating a detected signal in response thereto;
    fiber optic coupler for directing a portion of the optical beam onto the surface of the fluid, for directing another portion of the optical beam to the photo sensor, and for directing optical energy reflected from the surface to the fluid to the photo detector;
    phase sensitive detector;
    differentiator to differentiate the detected signal to produce a differentiated signal; and
    means for coupling the differentiated signal to the phase sensitive detector.

2. The apparatus of claim 1 wherein the means for generating comprises a frequency generator for generating a drive signal of a selected frequency coupled to a blade assembly positioned in close proximity to the surface of the fluid.

3. The apparatus of claim 2 further comprising a frequency doubler coupled to the frequency generator to generate a reference signal with a frequency two times the frequency of the drive signal and with a second harmonic having a frequency four times the drive signal frequency, and means for coupling the reference signal to the phase sensitive detector.

4. The apparatus of claim 1 wherein the fiber optic coupler reflects a portion of the optical beam off of a fiber optic end to the photo sensor.

5. The apparatus of claim 1 further comprising a full wave rectifier to rectify the differentiated signal to produce a rectified signal and means for coupling the rectified signal to the phase sensitive detector.

6. The apparatus of claim 5 wherein the phase sensitive detector phase compares the rectified signal to the second harmonic to obtain a phase difference.

7. The apparatus of claim 1 further comprising means for adjustably holding the fiber optic coupler in fixed relationship with the means for generating a surface wave.

8. The apparatus of claim 1 wherein the means for generating a surface wave comprises two orthogonal blades, each blade capable of being independently driven to generate surface waves.

9. A method for monitoring the surface of a fluid comprising the steps of:
generating a surface wave on the surface of the fluid;
producing an optical beam of optical energy;
detecting optical energy and generating a detected signal in response thereto;
directing a portion of the optical beam through an optical fiber onto the surface of the fluid, directing another portion of the optical beam to the photo sensor, and directing optical energy reflected from the surface of the fluid through the optical fiber to the photo detector;
differentiating the detected signal to produce a differentiated signal; and
coupling the differentiated signal to a phase sensitive detector.

10. The method of claim 9 wherein the steps of generating comprises generating a drive signal of a selected frequency coupled to a blade assembly positioned in close proximity to the surface of the fluid.

11. The method of claim 10 further comprising the steps of generating a reference signal with a frequency two times the frequency of the drive signal and with a second harmonic having a frequency four times the frequency of the drive signal, and coupling the reference signal to the phase sensitive detector.

12. The method of claim 9 further comprising the steps of rectifying the differentiated signal to produce a rectified signal and coupling the rectified signal to the phase sensitive detector.

13. The method of claim 12 further comprising the steps of phase comparing the rectified signal to the second harmonic to obtain a phase difference.

14. The method of claim 13 further comprising the step of determining a surface tension of the fluid using the phase difference.

15. The method of claim 14 wherein the step of directing a portion of the optical beam to the photo sensor comprises reflecting a portion of the optical beam from an end of the optical fiber to the photo sensor.

* * * * *